United States Patent [19]

Lloyd

[11] 4,367,609

[45] Jan. 11, 1983

[54] USE OF MICROORGANISMS IN CONJUNCTION WITH SEEDS

[75] Inventor: John M. Lloyd, Richmond, New Zealand

[73] Assignee: Coated Seed Limited, Christchurch, New Zealand

[21] Appl. No.: 283,338

[22] Filed: Jul. 14, 1981

[30] Foreign Application Priority Data

Jul. 28, 1980 [NZ] New Zealand .................. 194466

[51] Int. Cl.³ .............................................. A01C 1/06
[52] U.S. Cl. ...................................... 47/57.6; 71/6; 71/7; 47/DIG. 9; 111/DIG. 1
[58] Field of Search ................. 47/57.6, 58, DIG. 9; 71/6-7; 111/DIG. 1

[56] References Cited

U.S. PATENT DOCUMENTS

| | | | |
|---|---|---|---|
| 3,499,748 | 3/1970 | Fraser | 71/7 |
| 3,703,404 | 11/1972 | Kirk | 47/57.6 X |
| 4,136,486 | 1/1979 | Franklin et al. | 47/58 |
| 4,149,869 | 4/1979 | Lloyd | 71/7 |
| 4,155,737 | 5/1979 | Dommergues et al. | 71/7 |
| 4,229,544 | 10/1980 | Haynes et al. | 47/57.6 X |

*Primary Examiner*—Robert E. Bagwill
*Attorney, Agent, or Firm*—Scully, Scott, Murphy & Presser

[57] ABSTRACT

The survival of micro-organisms when used in conjunction with a seed is markedly improved by using a water soluble polyvinyl-pyrrolidone in conjunction with the micro-organism. The invention is illustrated by legume seeds inoculated with an appropriate rhizobia bacteria.

37 Claims, No Drawings

USE OF MICROORGANISMS IN CONJUNCTION WITH SEEDS

BACKGROUND OF THE INVENTION

1. Field of the Invention

This invention relates to seed coating techniques more particularly of coating seeds of plant species which enter into a symbiotic relationship with micro-organisms or else are beneficially effected by micro-organisms.

2. Prior Art

The desirability of inoculating legume seeds with an appropriate strain of rhizobia for the purpose of promoting plant growth is now well established. In fact in some countries such as New Zealand it is considered desirable for certain legume seeds to be inoculated with an effective strain of rhizobia bacteria before sowing. The primary effect of rhizobia bacteria is in the fixation of atmospheric nitrogen into a useable form of nitrogen for the plant. The rhizobia bacteria form nodules on the plant roots and are sustained by the plant and in turn provide nitrogen for the plant as mentioned above. Other micro-organisms do not enter into such a close symbiotic relationship with a plant but nevertheless when in close proximity to a plant can stimulate plant growth. Micro-organisms such as mycorrhizal fungi assist plant roots to absorb nutrients from the soil. Other plant growth assisting micro-organisms include but are not limited to *Azotobacter, Bacillus spp* and much research is continuing with other forms of such micro-organisms.

The effectiveness of rhizobia is now well documented as is the effectiveness of certain brands of commercially inoculated and coated seed. With other micro-organisms the effectiveness is not quite so marked but nevertheless this invention is considered as being applicable to the use of such other micro-organisms as well.

It has been found over a number of years, and there are many reports in the literature on such observations, that seeds possess certain substances which are toxic to micro-organisms. This effect has been particularly noted with the more actively researched legume seeds and the corresponding rhizobia bacteria. Certain researchers have characterised some of the toxins and have been able to show that such toxins possess antibiotic activity in vitro against species of rhizobia. However the precise nature of all of the toxins in legume seeds is still the subject of some discussion in the literature.

To attempt to reduce the effect of toxins on micro-organisms such as rhizobia, a number of materials have been proposed to attempt to absorb or deactivate the toxins and thus prolong the life of the bacteria when present on the seed. Previously tried materials include charcoal, skim milk, casein, gelatin, glycerol, sucrose/yeast, sodium and other salts of casein and an insoluble polyvinyl-polypyrrolidone. Caseinate salts such as the sodium salt have shown useful improvement in rhizobia survival when used as an adhesive to bind coating materials including inoculant to the seed. The literature also reports tests on rhizobia survival in laboratory trials using an insoluble polyvinyl-polypyrrolidone sold under the trademark Polyclar AT by GAF Corporation (C.N. Hale Proc. N.Z. Grasslands Association Nov. 2-4, 1976 and Hale et al N.Z.J. Ag.Res. 20: 09-77).

Polyclar AT is defined by the manufacturers as polyvinyl-polypyrolidone and is an insoluble high molecular weight polymer. Its insoluble nature is no doubt in part created by the fact that it is cross linked. Hale reported the use of Polyclar AT, to inhibit the antibiotic activity of seed diffusates against isolates of Rhizobium species on agar cultures. The correlation between such in vitro trials and the effectiveness of such a material in assisting the survival of Rhizobium species on seeds is questionable. To be of any commercial use, the "detoxicant" must increase the survival of the rhizobia on the seed to a substantial extent to justify the additional costs involved in incorporating the material on the seed. Hale et al in the N.Z.J. Ag.Res. did measure the survival of rhizobia on seed in which Polyclar AT was mixed with white clover seed before inoculation and then inoculated and tested after 24 hours storage for survival of the bacteria. The amount of insoluble PVPP employed was 10% (w/w) of the seed. With such a treatment Hale et al reported that only 2.7% of the rhizobia bacteria survived after 24 hours in comparison with 0.3% with the control method.

The additional cost of the insoluble PVPP at such a concentration would be prohibitive and the apparent advantage achieved would be so minor as to be insignificant. In the experimental procedures of testing for numbers of rhizobia, the errors involved are so large that it is only after a statistically significant number of experiments can one say that 3% rhizobia survival is indeed different from 0.3% rhizobia survival.

The 1979 issue of the GAF Chemical Catalogue does state that the product identified as PVP/K-15 having an average molecular weight of about ten thousand does detoxify many poisons and irritants. However there is no mention that it can be used on seeds to improve the survival of micro-organisms which may have a beneficial effect on the seed.

As mentioned above the nature of the toxins that are exuded by seeds are still not totally defined. Moreover from the Hale et al article it is clear that the antibiotic effect of a seed diffusate in vitro can be stopped completely with Polyclar AT but when such a product is present in the seed coating the results which doubtfully indicate any significant improved survival of rhizobia bacteria.

Another article which does mention the use in general terms of polyvinyl-pyrrolidone is the Russian Chemical Review 43 (7) 1974 which reported that the quality of an applied coating of pesticides to a seed can be improved by introducing a polymeric film forming agent into the composition. One example is given of incorporating up to 15% of polyvinyl-pyrrolidone in the coating. The article does not clearly state whether the PVP being referred to is of the soluble or insoluble form and more importantly no mention is made that they are concerned with legume seeds or the problem of survival of rhizobia bacteria or any other micro-organisms on or used in conjunction with seeds.

Thus there has been a problem in the seed industry of being able to market a seed pre-inoculated with rhizobia bacteria to allow for inherent delays in marketing and freight and still ensure that sufficient rhizobia survive to perform their necessary function. In situ inoculation, namely where the farmer himself applies a culture of rhizobia bacteria to legume seeds immediately before sowing, has still therefore been widely practised to ensure that sufficient rhizobia bacteria are present at time of sowing.

Despite the fact that knowledge has existed in the art of the toxicity of certain materials in seeds to the symbiotic bacteria and attempts at reducing the toxic effects by using certain additives has been actively researched, the degree of improvements reported in the literature has been small.

SUMMARY OF THE INVENTION

This invention is based on the surprising discovery that the use of a water soluble polyvinyl-pyrrolidone (herein referred to as water soluble PVP) markedly improves the survival of rhizobia on a legume seed. The exact mechanism by which the water soluble PVP does improve the survival, is not known to the applicant but it is thought that it is the result of an inhibition of the natural antagonism between the rhizobia and the toxic exudates from the seed previously referred to. The invention therefore provides for the use of a water soluble PVP in association with a seed to promote the survival rate of a micro-organism which is applied to the seed or used in association with the seed at the time of planting.

Thus in its broadest aspect the invention provides in a method of sowing seeds in which a micro-organism is present for the purpose of promoting some desired effect to the seed or in conjunction with the seed, the improvement comprising using a water soluble polyvinyl-pyrrolidone to promote the survival of the micro-organism.

The invention also provides a seed having an external coating comprising a micro-organism and a water soluble polyvinyl-pyrrolidone.

The water soluble PVP for use in this invention can be that as generally supplied to commence in different molecular weight grades. Each grade is generally categorised by reference to a K value. For example K-15 has an average molecular weight (ave. MW) of 10,000, K-30 an ave. MW of 40,000, K-60 an ave MW of 160,000 and K-90 an ave MW of 360,000. Preferably for reasons of cost and availability the PVP will have an average molecular weight of less than 400,000.

In preferred methods of this invention as described herein below fine spraying of a PVP solution is desirable. In such methods it is desirable for the viscosity of the solution to be low. The higher the K value of PVP the higher the viscosity of a solution.

The preferred forms of PVP for use in this invention are thus the lower viscosity grades having a molecular weight less than 100,000 for example K-30 and K-15.

The invention is primarily concerned with, and will be so described with reference to, the use of a water soluble PVP in association with a legume seed in order to promote the survival of rhizobia bacteria applied to or used in conjunction with the legume seed. However the primary effect of the water soluble PVP is to promote the survival of rhizobia by apparently reducing the antagonistic effect of the toxic exudates of the seed on the bacteria. Thus the invention includes the use of a soluble PVP with any micro-organism which is to be applied to or along with a seed where the survival of that micro-organism is adversely effected when applied to or used with an untreated seed. The invention covers methods in which the micro-organism is incorporated in or forms a coating on a seed or is applied to the locus of the seed at the time of planting the seed in such a manner as to be in sufficiently close relationship to the seed to perform its desired function.

With these points in mind, the specification will describe the effect of using soluble PVP in the system of a legume seed and a rhizobia bacteria. In such systems legume seeds and their corresponding symbiotic rhizobia bacteria include white clover seed (*Rhizobium trifolii*,) lucerne seed (*Rhizobium meliloti*) and subterranean clover (*R. trifolii*).

In inoculating legume seeds with rhizobia bacteria the inoculant has either been applied to a seed for immediate useage or has been incorporated in a coating on the seed along with the adhesive used to bond other coating materials such as lime, to the seed. Such latter materials have enabled inoculated seeds to be marketed commercially. The shelf life of such inoculated seed has been two to four weeks. In both of these prior art techniques the inoculant has generally been in the form of a slurry of a carrier medium (containing the rhizobia bacteria) in water. In the commercial coating method a drying step has been required after coating of the seed which does create difficulties in view of the low resistance of the rhizobia bacteria to high temperature. Low temperatures have had to be employed causing longer drying times and hence increased throughput times.

In our United Kingdom Patent Specification No. 1465979 a method was described in general terms whereby an absorbent coating was first formed on a seed and this absorbent coating then used to absorb effective agricultural chemicals in a continuous state. One suggestion was absorbing a slurry of rhizobia bacteria. In such a method provided the absorbency of the coating and the moisture content in the slurry was predetermined, the slurry could be absorbed onto a predetermined amount of coated seed to form free flowing coated seeds which would not require a further drying step. The applicant has found that in the formation of the pre-coated seed, the toxins in the seed are mobilized and penetrate into and through the coating. When the slurry of bacteria is applied, while the initial rhizobia counts are high, there is a rapid deterioration in their number such that the shelf life of such material was generally less than two weeks. The soluble PVP as used in accordance with the invention provides markedly improved rhizobia survival when incorporated in the inoculant slurry or applied to the seed along with the inoculant slurry. Substantial improvement in rhizobia survival occurs in comparison to control methods (in which no soluble PVP is employed) when a slurry of an inoculant in an aqueous solution of PVP is applied to bare seed or to previously coated seed. Such methods therefore form preferred methods of the invention.

Furthermore it is known at present to market inoculants in carrier media which maintain the rhizobia in a viable state or can be such as to allow for multiplication of the bacteria.

This invention therefore also provides an inoculant comprising a species of Rhizobium together with a soluble form of polyvinyl-pyrrolidone.

As mentioned above rhizobia inoculants are generally comprised of strains of the appropriate species of Rhizobium mixed with a carrier medium. The usual carrier employed is peat having its pH adjusted to between 6.5 and 7 generally with lime or other suitable alkaline material.

The preparation of the inoculant involves selection of a suitable strain of the Rhizobium species. In New Zealand high quality strains are held by the Plant Disease Culture Division of the Department of Scientific and Industrial Research under numbers 2668 and 2153

(*R. trifolii*) generally used in admixture, and 2751 and 2752 (*R. meliloti*) again generally used in admixture and these are the desired rhizobia strains for use in this invention.

The freeze dried culture obtained from the culture collection are cultured to form a mother culture from which sub-cultures can then be grown. The sub-culture is then added under sterile conditions to the sterile carrier medium in order to ensure the material does not contain contaminating organisms and packed under sterile conditions into a sealed envelope such as high density polyethylene. The currently recommended shelf life for such envelopes is of the order of 3 months but the shelf life can be increased if the envelopes of the inoculant are stored at low temperatures such as in a cool store at 3° to 5° C.

The inoculant as produced by the Inoculant Division of TNL Group Limited of Nelson, New Zealand under the trademark "Rhizocote" generally contains of the order of $5 \times 10^9$ rhizobia bacteria per gram of inoculant. Much higher bacteria counts may be achieved in certain circumstances such as of the order of $1 \times 10^{10}$ bacteria per gram.

The generally recommended proportion of inoculant to bare seed is to use one sachet of inoculant of 160 grams to coat 25 kilograms of seed. Obviously in certain situations it may be desirable to increase the amount of inoculant but reduction in the amount is not recommended as then nodulation of the treated seed may not be as satisfactory.

By the invention the PVP is preferably packaged in a separate sachet from the inoculant with instructions for the end user to dissolve the PVP in water and use that solution at a pre-determined concentration of PVP to form the slurry of the rhizobia inoculant.

It is desirable for known reasons to coat the seed such as to improve ballistic properties and germination or to incorporate materials which assist plant growth. Such materials include lime, rock phosphates, bauxite, reverted superphosphate and dolomite, which are adhesively bound to the seed. It is within the scope of the invention for substantial amounts of such materials to be applied to the seed as more particularly described and claimed in applicants United Kingdom Specifications Nos. 1380865 and 1479848.

The adhesive used can be those as described in United Kingdom Pat. Nos. 1380865 and 1479848 such as gum arabic, carboxymethyl-cellulose and alginates and also the adhesives described in U.S. Pat. No. 4149869, namely soluble caseinate salts such as sodium casinate. The adhesive used is desirably water soluble to allow redispersion of the coating.

It is important within this invention to monitor the absorbency of the coating and the amount of water in the inoculant slurry. If excess water is present in the slurry over and above the absorbency of the coating, absorption of water by the seed can occur leading to premature initiation of the germination process. Toxic substances are consequently released from the seed in the presence of this excess moisture and to the detriment of the rhizobia. In addition excess moisture will cause dissolution of the adhesive and subsequent softening and shedding of the coating on the seed.

The coating on the seed in this form of the invention will thus need to be of some absorbency but where the absorbency is low the water content in the slurry will need to be kept to a minimum. The provision of a coating of a finely divided absorbent material on a seed which is then used to absorb a slurry of agriculturally effective micro-organisms is fully discussed in the specifications of United Kingdom Pat. No. 1465979 and such techniques as are discussed therein can be utilized within the terms of this invention. The absorbency of the coating within the terms of this invention does not need to be high and coating materials such as those mentioned previously have a satisfactory absorbency within the terms of the invention.

In the aforementioned United Kingdom Specification No. 1465979 a preferred method to form the pre-coating of the powder on the seed was to first moisten the absorbent powder with water to satisfy the absorbency, bond the powder onto the seed with the adhesive and then dry the thus coated seed to evaporate the excess moisture in the powder to return the powder to substantially its original absorbency. This method had two effects firstly in order to reduce the amount of adhesive required and secondly to obtain a substantially uniform absorbency of each seed coating. While this method can be used in accordance with this invention, this invention also provides another method of obtaining a physically stable and still absorbent coating on the pre-coated product prior to addition of the inoculant slurry. This method comprises firstly loosely coating the seed with adhesive and the coating material and then compacting the loose coating on the seed using a water spray in a rolling cylinder. The initial blending comprises mixing the adhesive with the raw seed in a blender and when the adhesive is evenly distributed, adding the coating material and continuing blending until the seeds have separated and become loosely coated. The period of blending will vary according to the seed species, characteristics of the coating material and type of blender used. The time taken to blend the coating material with the seed is critical. If the blending time is too short the seeds are unevenly coated and conglomerates of seed occur. If the blending time is excessive coating material and adhesive will be removed permanently from the seed. Experience alone will determine the optimum blending time for a particular product, but in general the difference between an insufficient and excessive blending time will be measured in seconds.

In the second stage of the process, the amount of water applied can vary dependent upon the seed and other factors. Generally the amount will lie within the range of between 1 to 8 liters per 100 kilos of raw seed but in certain situations greater or lesser amounts of this may be required. The loosely coated seeds from the first stage are rolled in the rolling cylinder for a period of time until satisfactory compaction occurs. Again this is a matter dependant upon the various materials used and a skilled operator will be able to judge in any particular case when compaction is complete. A time of the order of 10 minutes would be a general guideline as to the time required for compaction to occur.

After compaction the pre-coated seeds are then dried. The so dried seeds can then be used to absorb the inoculant slurry.

The inoculant slurry is then added to the pre-coated seed. The inoculant culture can be a broth inoculant, a broth inoculant transferred to a free flowing peat medium, an inoculant grown in a free flowing peat or other medium, or an inoculant freeze dried (lyophilised) culture mixed with water. The carrier medium can be a growth supporting medium to encourage multiplication of the rhizobia or can be such as to maintain the bacteria in a viable state. The inoculant is mixed with sufficient water to provide the slurry. In the most preferred form of the invention the soluble polyvinyl-pyrrolidone is dissolved in the aqueous slurry and this slurry is applied to the pre-coated seed.

Before application of the slurry to the seed it is important to thoroughly disperse the inoculant in order to achieve adequate distribution on the seed subsequently and also to prevent blockage occurring in the application equipment such as spray nozzles. The Rhizobia bacteria on the other hand can be damaged during prolonged or severe stirring. It is therefore important to controlled stirring. Satisfactory dispersion of the inoculant can be achieved by means of a Silverson heavy duty type laboratory mixer (Model L2R) fitted with a disintegrator type head. For example a batch of inoculant slurry prepared from 5.72 kg of 24.5% PVP solution and 1.28 kg Rhizocote (Registered trademark) inoculant in a 10 liter capacity open mouth bucket is placed under the Silverson mixer which is operated for 8 minutes at maximum speed.

The inoculant slurry can then be applied to the pre-coated seed. Because of the factors mentioned above in regard to monitoring the absorbency of the coating-/moisture content in the slurry, the absorbency in the coating is generally provided as being in excess of that required to take up the moisture and other material in the inoculant slurry. In order to achieve a substantially uniform amount of the inoculant on each seed, the application of the slurry is applied in a manner that allows the maximum contact of each seed with the slurry. Spraying of the slurry is therefore desired and at the same time rolling the seeds within a rolling cylinder. A most desirable manner of spraying in the inoculant slurry is to use air atomizing nozzles with an automatic self cleaning needle.

The materials used to coat seed are preferably of a type that assist the survival of micro-organisms on the seed and have a beneficial effect after the seed is sown. For example peat may be used in admixture with lime to reduce pH and provide a more favourable environment for rhizobia. A lime coating increases the chance of securing successful nodulaton under relatively difficult conditions such as when inoculated legume seed is sown into acid soil or mixed with acidic fertilizer for aerial sowing. Nutrient materials such as lime reverted superphosphate can be used to assist seedling growth.

All of the materials in the coating are finely ground in order to achieve good uniformity of product, good adhesion to the seed and good dispersability when the seed is sown. The fineness is desirably of a size such that the particles pass a 150 mesh BSS more desirably where approximately 95% pass a 300 mesh BSS. The limestone can for example be that provided as "Green Square" by Mintech N.Z. Ltd.

After application of the inoculant slurry to the coated seed, further materials as desired can be added. Such materials can for example be added to improve the appearance of the product and also as a sunlight absorber to prevent possible damage caused by ultra-violet light. A desirable material has been found to be kaolin pH adjusted to a satisfactory pH for the rhizobia bacteria such as by combination with lime. A certain type of kaolin namely "Ultra Fine China Clay" produced by N.Z. China Clays Ltd has been found to have an adhesive character of its own and is thus able to adhere to the inoculated coated seed without the requirement for additional adhesive.

The soluble PVP used in accordance with the invention is present in an effective amount to improve the survival of rhizobia or other micro-organism. The amount that one can use is dependant upon a number of variables particularly the type of legume seed being employed. The PVP of a soluble nature has been found to markedly increase the survival of applied rhizobia bacteria.

Increased rhizobia survival is noticeable at low percentage rates of the soluble PVP in comparison to the raw seed weight. Increasing the amount of soluble PVP above a certain level does not produce a corresponding improvement in rhizobia survival. Moreover increasing the amount of PVP above a certain level increases the viscosity of such a solution to a degree where it becomes difficult to spray which is the preferred method of application of the PVP. Thus the maximum amount of PVP that will be employed in this invention is dictated by the viscosity factor and also by a question of the cost of the material. Satisfactory results have been achieved using soluble PVP in amounts from 0.5% to 1.5% by weight of the raw seed. It is obviously within the scope of the invention for higher amounts to be used but because the survival of rhizobia is so markedly improved through the use of such relatively small amounts of PVP the preferred alternative to achieving higher rhizobia counts would be to increase the amount of inoculant rather than increasing the proportion of PVP.

The amount of coating material applied to the seed initially will depend upon the type of end product required. Thus the coating can vary from less than the weight of the seed up to 30 times the weight of the seed.

The preferred method of the invention comprises pre-coating the seed with a coating of a material which is absorbent to the required degree, drying to remove excess moisture, and then applying an inoculant slurry of a culture of rhizobia in a peat medium in a solution of PVP in water. There are several advantages in separating the application of the powder coating from application of the inoculant to the seed. The first advantage is that the drying conditions for the pre-coated seed can be much more stringent than when the bacteria are present in the coating.

Rhizobia bacteria have a high mortality at high temperatures and thus drying a coated seed which contains rhizobia bacteria either results in considerable mortality of the rhizobia or else because of the low temperatures of drying longer times and low through put times result. The initially pre-coated seed can be dried at higher temperatures than for seeds having the rhizobia in the coating and consequently through put times can be reduced.

The second advantage which is of considerable importance for a commercial process is that inoculation by the inoculant media can take place at a separate location from the initial pre-coating. Whilst the use of water soluble PVP within the terms of the invention in the coating does increase markedly the useful life of the inoculated seed, nevertheless it is still a limited period. Inoculated seed prepared by the preferred process of the invention can be sold as such having a useful life of the order of 8 to 16 weeks. However freighting of coated seed from a central location to the consumer at various places in one country or to another country relies on freight being delivered within the schedule desired. Delays in delivery are a fact which must be taken into account. Also there will be considerable temperature fluctuations in transport which again have a material effect on the survival of the bacteria. There is the further problem that processing must be carried out substantially near or during the time of sowing. As a consequence manufacturing plant will be heavily used at a particular period of the year and for the remainder of the year may remain idle. The capital cost of the equipment to pre-coat the seed is substantially greater than the equipment required for inoculating the plant seed. By providing a central pre-coating plant, the pre-coated seeds can be prepared at a reasonably uniform rate throughout the entire year to provide the volume required at the peak use period, such pre-coated seeds then freighted to a location or various locations close to consumers throughout a particular country or to another country and when demand during the peak season commences inoculation can be carried out and the product rapidly delivered to the close at hand consumers. Shipping the pre-coated seed for the longer distances means that mortality of rhizobia caused by rising temperature and/or ageing is avoided and fresh inoculated seed is supplied to the consumer.

The quantity of inoculant applied is calculated to be sufficient for effective nodulation and enable the coated inoculated seed to meet any standard prescribed by official agencies. The official standard in New Zealand is a minimum of 300 viable rhizobia per seed. By this invention substantially higher rhizobia counts can be achieved both initially (in comparison to techniques which involve drying of applied rhizobia) and also after a period of time after inoculation.

Using "Rhizocote" inoculant a satisfactory proportion of seed to the inoculant/PVP mixture is in the proportion of 100 parts of the pre-coated seed to 2 parts of the inoculant/PVP slurry. Larger amounts of inoculant can be used if desired.

The amount of a PVP in the inoculant slurry varies as mentioned above primarily in relation to the volume of seed but can also vary in relation to the amount of inoculant. A suitable ratio of "Rhizocote" inoculant to PVP is about one part of "Rhizocote" inoculant to one part of PVP.

The following example illustrates the process of preparing the product of the invention:

EXAMPLE 1

100 parts of white clover seed in a blender are mixed with 20 parts by weight of a 12.5% solution of sodium caseinate as an adhesive until the adhesive is evenly distributed. 75 parts by weight of a mixture of 89.5% finely ground limestone (Green Square) and 10.5% finely ground peat are then added to the blender and blending continued until the seeds have separated and become loosely coated. The loosely coated seeds are then transferred to a rolling cylinder and sprayed with from 1 to 8 liters of water while rolling for approximately 10 minutes until satisfactory compaction of the coating is achieved. The seed is then transferred to a dryer and dried to remove the moisture.

100 parts by weight of this basic coated seed is then added to a rotating cylinder, and blended with two parts by weight of the inoculant/PVP slurry consisting of 0.366 parts by weight of Rhizocote (registered trademark) 0.4 parts of PVP (K-30) and 1.234 parts of water. This inoculant is sprayed by air atomizing nozzles onto the rotating pre-coated seed until even distribution has occurred. While continuing rotating in the rolling cylinder three parts by weight of a kaolin/lime mixture consisting of 1.8 parts of ultra-fine kaolin and 1.2 parts of lime is added.

The following example refers to field trials which were carried out to illustrate the effectiveness on growth establishment using the invention.

EXAMPLE 2

These experiments were carried out in accordance with procedures adopted by the New Zealand Ministry of Agriculture and Fisheries. In all experiments the basic coating was a peat/lime mixture using sodium caseinate as th adhesive. In experiments 1 and 2 the inoculant was incorporated along with the peat in the coated seed. No polyvinyl-pyrrolidone was used. In experiment 3 the peat/lime coat with caseinate adhesive was first formed on the seed in the manner described in the above example and then the inoculant together with polyvinyl-pyrrolidone in the amount mentioned above in the example was sprayed on. In experiment 4 again the peat/lime pre-coat was first formed with the caseinate adhesive. The coated seed dried and the inoculant slurry without any PVP was applied. In experiment 1 the coated seeds were prepared 44 days before planting while in all other 3 experiments the coated seeds were prepared 23 days before planting. Two separate sites with two replications at each site were used in each experiment. After 100 days the number of seedlings present in each plot were counted the average over the two plots at each site taken and then the average over both sites taken. The following results were obtained:

Experiment 1

24 seedlings.

Experiment 2

28 seedlings.

Experiment 3

68 seedlings.

Experiment 4

30 seedlings.

This experiment clearly demonstrates the resulting effectiveness of incorporating PVP in the coating on the seed.

EXAMPLE 3

A laboratory trial based on counting the number of rhizobia per white clover seed for the nominated periods of storage at 25° C. was also carried out. In each case the white clover seed was first coated with a lime/peat coating and then the inoculant slurry sprayed onto the pre-coated seed. The variation in each experiment was the material present in the inoculant slurry:

| Additive To Inoculant Slurry | 0 days | 3 days | 7 days | 14 days |
|---|---|---|---|---|
| Water | 10,000 | 600 | 200 | 57 |
| Caseinate | 33,000 | 3,000 | 600 | 330 |
| Glycerol Sucrose/ | 10,000 | 2,000 | 100 | 10 |
| Yeast Soluble | 10,000 | 1,100 | 330 | 100 |
| PVP | 11,000 | 11,000 | 11,000 | 2,300 |

EXAMPLE 4

Samples of coated white clover seeds were prepared. This coated seed was prepared in accordance with a procedure of Example 1. Soluble PVP/K-30 grade was used at a rate equivalent to 1% of the actual seed weight. The quantity of water applied with the inoculant slurry to the raw seed and to previously coated dry seed was equivalent to 2.16% of the actual seed weight in each case. Samples were tested for viable rhizobia by the plant infection method (MPN) the day they were produced and at seven day intervals thereafter. Samples were held at a constant 20° C. between tests to accelerate rhizobial mortality.

The following treatments were employed:
(1) Uncoated bare seed was inoculated with an aqueous suspension of inoculant without any PVP.
(2) As in (1) but PVP was added to the inoculant slurry.
(3) The seed was coated and inoculated with an aqueous suspension of the inoculant without using PVP.
(4) As in treatment (3) but PVP was present in the inoculant slurry. The following table I lists the results.

TABLE I

| | (thousands rhizobia/gram product, 95% fiducial limits are in parentheses) | | | |
|---|---|---|---|---|
| Treatment | 0 days | 7 days | 14 days | 21 days |
| 1 | 850 (220-3200) | 78 (21-300) | 43 (11-160) | 15 (4-57) |
| 2 | 2500 (660-9 500) | 1700 (450-6500) | 850 (220-3200) | 2500 (660-9 500) |
| 3 | 8500 (2200-32000) | 78 (21-300) | 15 (4-57) | 7.8 (2.1-30) |
| 4 | 2500 (660-9 500) | 1700 (450-6500) | 450 (120-1700) | 850 (220-3200) |

It is clear from this table that experiments 2 and 4 in which PVP was employed show much higher rhizobia survival than either experiments 1 and 3. Experiment 3 illustrates the rapid mortality of the rhizobia when applied to pre-coated seed which is of the same order as the mortality of bacteria applied to bare seed.

People in the art will recognize that it not possible to reach any firm quantitative conclusion on the effectiveness of any particular method on the basis of a single trial.

The applicant by this example and by Example 2 and by many other trials which it has carried out is able to firmly reach the conclusion that the number counts shown in Table 1 of rhizobia by the methods of the invention in comparison to the control methods are indicative of the improvement brought about by the method of the invention. By the method of the invention 100% of survival of rhizobia bacteria after 21 days has often been achieved. This is obviously many orders of magnitude greater than the 3% survival after 24 hours reported in the Hale et al paper in the prior art using insoluble PVPP.

To confirm the effectiveness of soluble PVP in comparison to insoluble PVPP as suggested in the Hale et al paper the following examples were carried out:

EXAMPLE 5

The Hale et al article reported best results when the insoluble PVP was first mixed with autoclaved white clover seed at a ratio of 10% by weight of the seed, the sample was moistened with sterile distilled water, dried at 50° C. and then inoculated and tested for viable rhizobia as above.

This method was repeated by the applicant. A problem existed with the method of Hale in that the Polyclar AT did not have any adhesive effect and separated from the seed. In a field situation, the Polyclar AT would thus naturally separate from the seed and then would have no further effect on the seed. Hence in this repeat of Dr Hale's treatment, the Polyclar AT was separated from the seed immediately prior to testing by passing the mixture over a sieve. It is the number of rhizobia on the seed that is important not the number of rhizobia present on the Polyclar AT. Comparisons were made with the following treatments:
(1) The seed was coated by the method of Example 1, dried and then inoculated with "Rhizocote" (trademark) inoculant dispersed in an aqueous solution of PVP K-30 to give 1% PVP on actual seed weight,
(2) As in (1) but the inoculant dispersed in water only with no PVP,
(3) As for (2), but Polyclar AT was incorporated in the coating at a rate equivalent to 2.5% of the actual seed weight.
(4) As for (3) but 10% Polyclar AT.
(5) Repeat of Dr Hales method described above.

The following table provides the results. The samples were tested for survival of rhizobia by the plant infection method (MPN) the day they were inoculated and at seven day intervals thereafter. Samples were held at a constant 20° C. between tests.

TABLE II

| | (thoudands rhizobia/gram product. 95% fiducial limits in parenthesis) | | | | |
|---|---|---|---|---|---|
| Treatment | 0 | 7 days | 14 days | 21 days | 28 days |
| 1 | 4500 (1200-17000) | 1700 (450-6500) | 8500 (2200-32000) | 2500 (600-9 500) | 850 (220-3200) |
| 2 | 4500 (1200-17000) | 15 (4-57) | 78 (21-300) | 78 (21-300) | 25 (6-95) |
| 3 | 1700 (450-6500) | 25 (6-95) | 250 (66-9-50) | 450 (120-1700) | 78 (21-300) |
| 4 | 1700 (450-6500) | 25 (6-95) | 78 (21-300) | 78 (21-300) | 78 (21-300) |
| 5 | 850 (220-3200) | 150 (40-570) | 250 (66-9 50) | 43 (11-160) | 43 (11-160) |

From Table II the use of Polyclar AT can possibly be said to marginally increase rhizobia surival over a treatment without Polyclar AT but the errors involved make such conclusions dubious. On the other hand the treatment with soluble PVP at lower rates of use clearly demonstrates a much superior effect.

EXAMPLE 6

The following trials were carried out to compare the method of the invention with a previous commercial method in which the inoculant was incorporated with the adhesive along with coating materials and then the coated seed dried. In the following table "STD" means this commercial method while "INV" means the method of the invention. In these trials the seeds were inoculated with exactly the same ratio of Rhizocote (registered trademark) inoculant to the weight of seeds. The results are expressed as MPN after the designated periods of storage at a constant 25° C. to accelerate rhizobia mortality.

TABLE III

| Seed Species & Method of Inoculation | (rhizobia/seed) | | | | |
|---|---|---|---|---|---|
| | Immed. | 7 Days | 14 Days | 21 Days | 28 Days |
| White Clover STD | 2565 | 256 | 150 | 150 | 150 |
| White Clover INV | 52940 | 5060 | 1765 | 2950 | 200 |
| White Clover STD | — | 370 | 370 | 630 | 370 |
| White Clover INV | — | 13450 | 4310 | 4310 | 1460 |
| Lucerne STD | 16350 | 165 | 95 | 15 | 10 |
| Lucerne INV | 60000 | 10000 | 600 | 600 | 310 |
| Lucerne STD | 3715 | 120 | 20 | 5 | 10 |
| Lucerne INV | 19550 | 19550 | 1550 | 1550 | 2050 |

It is clear that the drying of the standard inoculated seed caused substantial deterioration on the initial rhizobia counts.

Furthermore the survival of the rhizobia inoculated on the seed by the method of the invention was higher by a significant amount than the seeds inoculated by the standard method.

What we claim is:

1. In a method of sowing seeds in which a micro-organism is present for the purpose of promoting a desired effect on the seed or in conjunction with the seed, the improvement comprising using a water soluble polyvinyl-pyrrolidone to promote the survival of the micro-organism.

2. A method as claimed in claim 1 in which the water soluble polyvinyl-pyrrolidone is present as part as an external coating on the seed.

3. A method as claimed in claim 2 in which the seed is first coated with an absorbent material, which absorbent coating is used to absorb a slurry of the micro-organisms in an aqueous solution of polyvinyl-pyrrolidone.

4. A method as claimed in claim 1 in which the micro-organism is a Rhizobium bacteria and the seed is a legume seed.

5. A method as claimed in claim 4 in which the Rhizobium bacteria and water soluble polyvinyl-pyrrolidone are present as a coating on the seed.

6. A method as claimed in claim 5 in which the polyvinyl-pyrrolidone in solution is added along with the inoculant to the seed.

7. A method as claimed in claim 1 in which the polyvinyl-pyrrolidone has an average molecular weight of less than 400,000.

8. A method as claimed in claim 7 in which the polyvinyl-pyrrolidone has an average molecular weight less than 100,000.

9. A method as claimed in claim 1 in which the seed is bare seed.

10. A legume seed having an external coating comprising a bacteria of a Rhizobium species and a water soluble polyvinyl-pyrrolidone.

11. An externally coated legume seed as claimed in claim 10 in which the legume is white clover and the Rhizobium species is *R. trifolii*.

12. A externally coated legume seed as claimed in claim 10 in which the legume is lucerne and the Rhizobium species is R. meliloti.

13. An externally coated legume seed as claimed in claim 10 in which the legume is subterranean clover and the Rhizobium species is *R. trifolii*.

14. A legume seed as claimed in claim 13 in which the polyvinyl-pyrrolidone has an average molecular weight less than 100,000.

15. A legume seed as claimed in claim 10 in which the soluble polyvinyl-pyrrolidone has an average molecular weight less than 400,000.

16. An externally coated legume seed as claimed in claim 10 in which the bacteria is present in a carrier medium.

17. An externally coated legume seed as claimed in claim 16 in which the carrier medium is peat.

18. An externally coated legume seed as claimed in claim 10 in which the external coating additionally contains a material selected from nutrient materials and a material to adjust the pH of the coat.

19. An externally coated legume seed as claimed in claim 18 in which the additional coating materials are absorbent and into which is absorbed a slurry of the Rhizobium bacteria in an aqueous solution of polyvinyl-pyrrolidone.

20. A method as claimed in claim 18 in which the polyvinyl-pyrrolidone is present in an amount of from 0.5% to 1.5% by weight of the raw seed.

21. A method of producing an externally coated legume seed in which the coating comprises a bacteria of a Rhizobium species and water soluble polyvinyl-pyrrolidone comprising forming a slurry of the bacteria in an aqueous solution of polyvinyl-pyrrolidone and applying the slurry to the seed.

22. A method as claimed in claim 21 in which the seed is bare seed.

23. A method as claimed in claim 21 in which the Rhizobium species is present in a carrier medium.

24. A method as claimed in claim 23 in which the carrier medium is peat.

25. A method as claimed in claim 21 in which the seed is first precoated with an absorbent material, selected from nutrients and pH adjusting agents, bonded to the seed with an adhesive, the absorbency of the materials and the water content in the slurry being selected so that the precoated seed can absorb completely the slurry of the bacteria in the aqueous solution of polyvinyl-pyrrolidone.

26. A method as claimed in claim 25 in which the absorbent coating is formed by first loosely coating the seed with adhesive and coating material and then compacting the loose coating on the seed by rolling the loosely coated seed in a rolling cylinder and spraying water into the cylinder.

27. A method as claimed in claim 25 in which the slurry of rhizobia bacteria in an aqueous solution of polyvinyl-pyrrolidone is applied to the pre-coated seed in such a manner as to allow maximum contact of each seed with the slurry.

28. A method as claimed in claim 27 in which the slurry is sprayed onto the pre-coated seeds and at the same time rolling the seeds within a rolling cylinder.

29. A method as claimed in claim 28 in which the spraying of the slurry is through air atomising nozzles with automatic self cleaning needles.

30. A method as claimed in claim 25 in which the coating materials are finely ground.

31. A method as claimed in claim 30 in which the coating materials are of a particle size less than 150 mesh BSS.

32. A method as claimed in claim 30 in which the materials are of a particle size such that 95% pass a 350 mesh BSS.

33. A method as claimed in claim 21 in which the Rhizobium bacteria are thoroughly dispersed within the slurry.

34. A method as claimed in claim 33 in which the Rhizobium bacteria are dispersed within the slurry by stirring in such a manner as to limit the damage to the bacteria.

35. A method of inoculating seeds comprising applying to a seed having an external coating of an absorbent powder material having no detrimental effect either on the seed or on Rhizobium bacteria, a slurry of a rhizobia bacteria in an aqueous solution of polyvinyl-pyrrolidone in such a fashion as to allow the coating to absorb uniformly the aqueous slurry.

36. An inoculant comprising a bacteria of a Rhizobium species and a carrier medium together with a water soluble polyvinyl-pyrrolidone.

37. A two pack inoculant comprising a pack of a bacteria of a Rhizobium species in a carrier medium and a second pack comprising a water soluble polyvinyl-pyrrolidone.

* * * * *